United States Patent [19]

Jubin, Jr.

[11] Patent Number: 5,468,885
[45] Date of Patent: Nov. 21, 1995

[54] EPOXIDIZER OXYGEN RECOVERY

[75] Inventor: John C. Jubin, Jr., West Chester, Pa.

[73] Assignee: ARCO Chemical Technology, L.P., Greenville, Del.

[21] Appl. No.: 365,397

[22] Filed: Dec. 28, 1994

Related U.S. Application Data

[63] Continuation-in-part of Ser. No. 310,546, Sep. 22, 1994, which is a continuation-in-part of Ser. No. 171,144, Dec. 20, 1993, abandoned.

[51] Int. Cl.$^6$ ...................... C07D 301/12; C07D 303/04
[52] U.S. Cl. ......................... 549/531; 252/372; 585/864
[58] Field of Search ........................... 549/531; 585/864; 252/372

[56] References Cited

U.S. PATENT DOCUMENTS

| | | | |
|---|---|---|---|
| 1,942,131 | 1/1934 | Baumann et al. | 585/864 |
| 2,189,062 | 2/1940 | Feiler | 585/864 |
| 2,642,154 | 6/1953 | Woodcock | 585/864 |
| 2,871,101 | 1/1959 | Rust et al. | |
| 2,871,102 | 1/1959 | Rust et al. | |
| 2,871,103 | 1/1959 | Skinner et al. | |
| 2,871,104 | 1/1959 | Rust. | |
| 3,777,928 | 12/1973 | Kober | 252/372 |
| 3,847,298 | 11/1974 | Hamilton | 252/372 |
| 4,824,976 | 4/1989 | Clerici et al. | 549/531 |
| 4,833,260 | 5/1989 | Neri et al. | |
| 5,262,550 | 11/1993 | Crocco et al. | |

Primary Examiner—Joseph E. Evans
Attorney, Agent, or Firm—William C. Long

[57] ABSTRACT

An olefin/oxygen purge gas from the catalytic reaction of the olefin with hydrogen peroxide is contacted with an absorbent liquid such as isopropanol and water to absorb olefin while an inert gas such as methane is added to avoid formation of flammable oxygen-containing gas compositions.

4 Claims, 1 Drawing Sheet

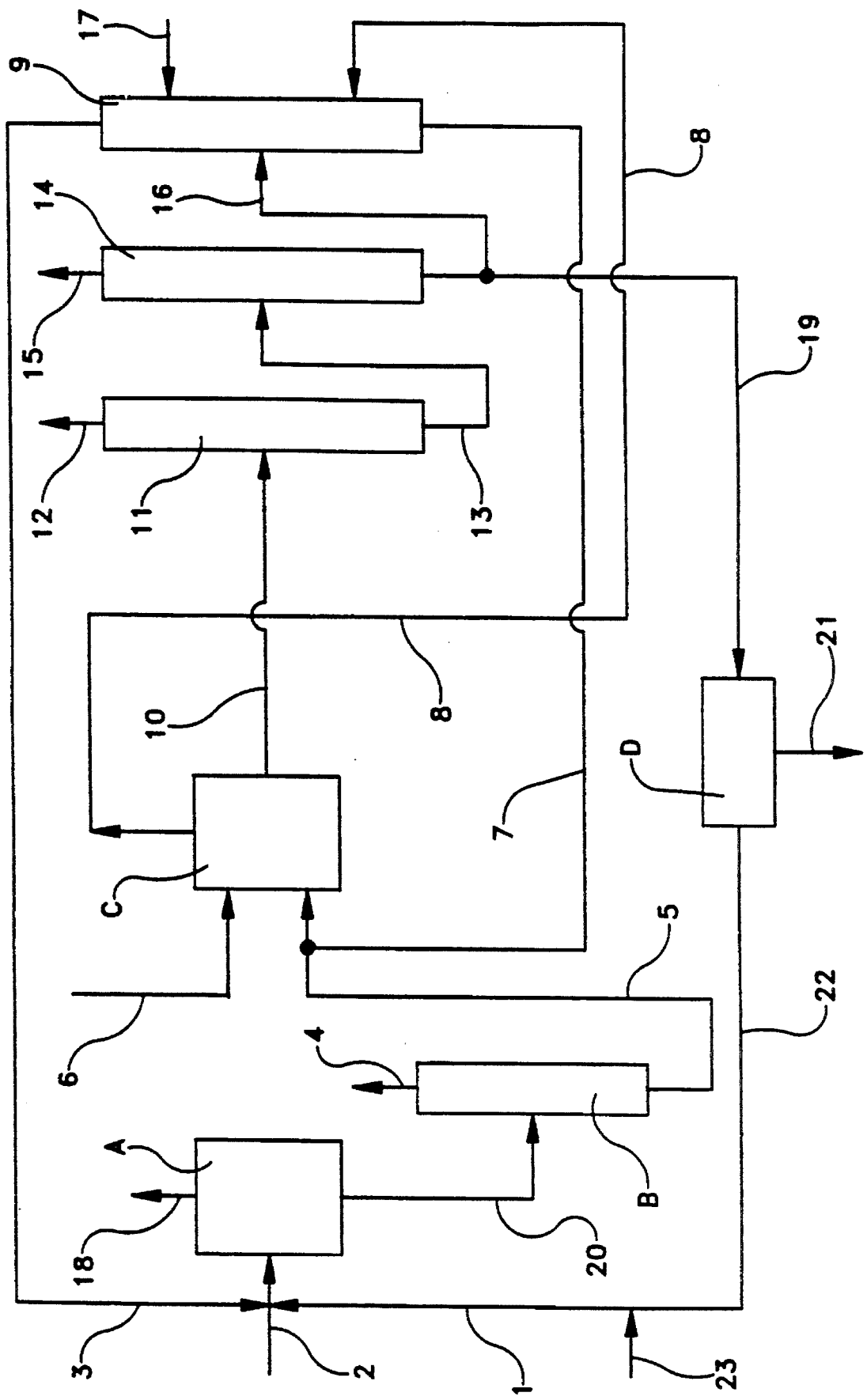

EPOXIDIZER OXYGEN RECOVERY

RELATED APPLICATIONS

This application is a continuation-in-part of application Ser. No. 08/310,546 filed Sep. 22, 1994 which is a continuation-in-part of Ser. No. 08/171,144 filed Dec. 20, 1993, now abandoned.

BACKGROUND OF THE INVENTION

1. Field of the Invention

The present invention relates to the recovery of oxygen which is formed by hydrogen peroxide decomposition during the epoxidation of an olefin such as propylene with hydrogen peroxide as well as recovery of associated olefin.

2. Description of the Prior Art

Methods are known for the molecular oxygen oxidation of a secondary alcohol to form hydrogen peroxide. See, for example, U.S. Pat. Nos. 2,871,101–2,871,104. See also copending application Ser. No. 08/268,891 filed Jun. 30, 1994.

Methods are also known for the catalytic epoxidation of olefins such as propylene with hydrogen peroxide to produce an alkylene oxide such as propylene oxide. See, for example, U.S. Pat. Nos. 4,833,260 and 5,262,550 as well as copending application Ser. No. 08/310,546 filed Sep. 22, 1994, the disclosure of which is incorporated herein.

As described in copending application Ser. No. 08/310,546, there is some hydrogen peroxide decomposition which takes place during the epoxidation with the formation of oxygen and this formed oxygen can be purged from the epoxidation reaction zone with, for example, propylene vapor in order to avoid the formation of hazardous mixtures.

In order to avoid a substantial economic penalty, it is important that the purge gas mixture from the epoxidation zone be safely and effectively treated for the recovery of the various components.

BRIEF DESCRIPTION OF THE INVENTION

In accordance with the present invention, the olefin/oxygen vapor purge stream from the epoxidation is contacted with a liquid absorbent stream, preferably a stream comprised of the secondary alcohol from which the hydrogen peroxide is formed, to absorb olefin therein and enable separation of gaseous oxygen from the liquid olefin-containing absorbent. In addition, an inert gas diluent such as methane is added to replace absorbed olefin in order to avoid the formation of oxygen-containing gas mixtures which are in the flammable range. In most preferred practice, the liquid olefin-containing absorbent stream is passed to the epoxidation zone and the oxygen-containing gas stream is passed to the secondary alcohol oxidation zone.

DESCRIPTION OF THE DRAWING

The attached drawing illustrates in schematic form an embodiment of the invention.

DESCRIPTION OF PREFERRED EMBODIMENTS

An especially preferred embodiment of the invention is illustrated in the accompanying drawing and involves the production of propylene oxide by catalytic reaction of propylene with hydrogen peroxide, the hydrogen peroxide being formed by oxidation of isopropanol.

Referring to the accompanying drawing, isopropanol and molecular oxygen are reacted in zone A to form hydrogen peroxide. The isopropanol is fed via line 23 (net feed) and recycle line 22 and passed to zone A via line 1. Oxygen is fed via line 2 and a recycle methane and oxygen stream is fed via line 3. Isopropanol oxidation is carried out in accordance with known procedures such as are described in U.S. Pat. Nos. 2,871,101–2,871,104. The process set forth in copending Ser. No. 08/268,891, filed Jun. 30, 1994 is especially advantageous.

The hydrogen peroxide containing reaction mixtures passes to separation zone B via line 20 wherein acetone produced in zone A is distilled overhead via line 4. The hydrogen peroxide stream passes to epoxidation zone C via line 5 for reaction to form propylene oxide. Propylene is introduced via line 6 and a recycle stream comprised of diluent isopropanol as well as and propylene is transferred to zone C via line 7.

In zone C, propylene and hydrogen peroxide are catalytically reacted to form propylene oxide in accordance with known reaction procedures. Suitable catalysts and reaction conditions are shown, for example, in U.S. Pat. Nos. 4,833,260 and 5,262,550 the disclosures of which are hereby incorporated by reference. An especially preferred epoxidation made is that described in copending application Ser. No. 08/310,546 filed Sep. 22, 1994.

A purge stream comprised of oxygen from hydrogen peroxide decomposition and propylene is removed from zone C via line 8 and passes to absorption zone 9. Propylene oxide-containing liquid epoxidation reaction mixture passes from zone C via line 10 to distillation zone 11 where unreacted propylene is separated overhead via line 12. This propylene stream is conveniently recycled to zone D (not shown). The bottoms stream passes via line 13 to distillation zone 14 and a product propylene oxide stream is recovered overhead via line 15. A bottoms isopropanol stream containing water formed in the epoxidation is divided with a portion passing via line 19 to distillation zone D for removal of water and heavies via line 21. Isopropanol passes from zone D via line 22 back to oxidation zone A. The remaining portion of the isopropanol stream from zone 14 passes via line 16 to absorption zone 9 wherein it is contacted with the purge propylene/oxygen vapor stream which passes to zone 9 from epoxidation zone C via line 8. In absorption zone 9, the liquid isopropanol and water mixture effectively absorbs propylene from the propylene/oxygen mixture, and the resulting liquid stream containing absorbed propylene is passed via line 7 to epoxidation zone C wherein the propylene is subjected to further epoxidation while the isopropanol provides desirable dilution of the hydrogen peroxide from zone 1 and thus enhances propylene oxide selectivity.

An important feature of the invention is the provision of inert gas diluent, preferably methane, which is introduced into zone 9 via line 17 in amount sufficient to avoid the formation of flammable oxygen vapor mixtures. Generally, at least 5 mols of inert per mol of oxygen is introduced into zone 9 via line 17, preferably at least 8 mols of inert per mol of oxygen is provided up to about 20 mols of inert per mol of oxygen.

The vapor stream illustratively comprised of methane and oxygen passes via line 3 to oxidation zone A for further hydrogen peroxide formation.

A vapor purge stream is removed from zone A via line 18 to prevent inert build-up.

It will be apparent that practice of the invention provides an efficient and effective way of safely separating oxygen which is formed by hydrogen peroxide decomposition without costly and elaborate fractionations using available process streams and effectively recycling both oxygen and propylene components of the epoxidizer purge stream.

The following example illustrates the invention.

Referring again to the accompanying drawing, about 111 mols/hr of an isopropanol stream is fed to oxidation zone A via line 1. This stream comprises about 68.5 mol % isopropanol, 30.6% mol % water and 0.9 mol % acetone. About 14 mols/hr of oxygen is fed to zone A via line 2 and about 3.3 mols/hr of a recycle oxygen/methane stream is fed to zone A via line 3. This stream is comprised of about 91.0 mol % methane and about 9.0 mol % oxygen.

In zone A, isopropanol is oxidized in the liquid phase at 150° C. and 140 psig to hydrogen peroxide. A purge vapor stream is removed from zone A via line 18 at the rate of about 3.6 mols/hr, this stream being comprised of about 83.3 mol % methane and 16.7 mol % oxygen.

A liquid reaction mixture stream is removed from zone A and passes via line 20 to separation zone B wherein by distillation an overhead acetone stream is separated via line 4 at the rate of about 69 mol/hr. This stream comprises about 21.7 mol % acetone, 55.1 mol % isopropanol and 26.1 mol % water and can be further treated (not shown) for separation of the various components.

A bottoms hydrogen peroxide stream passes via line 5 to zone C at the rate of about 54 mols/hr. This stream comprises about 35.2 mol % water,r about 22.2 mol % hydrogen peroxide, and about 42.6 mol % isopropanol. About 40 mols/hr of propylene are fed to zone C via line 6 and a recycle stream is passes via line 7 from absorption zone 9 to zone C at the rate of about 159 mols/hr. this recycle stream comprises about 5.7 mol % propylene, about 1.3 mol % acetone, about 57.2 mol % water, about 34.5 mol % isopropanol, about 1.3 mol % heavies and a trace of propylene oxide.

In zone C, propylene is reacted with hydrogen peroxide in the presence of a silicalite catalyst to produce propylene oxide. Reaction conditions are a temperature of 60° C. and a pressure of 205 psig.

Liquid reaction mixture passes from zone C via line 10 to separation zone 11. Unreacted propylene is recovered overhead at the rate of 37 mol/hr. and can be recycled to zone B (not shown).

Bottoms from zone 11 is passed via line 13 to distillation zone 14 at the rate of 225 mol/hr. This stream comprises about 4.4 mol % propylene oxide, about 1.3 mol % acetone, about 54.2 mol % water, about 38.7 mol % isopropanol and about 1.3 mol % heavies.

From distillation zone 14, a product propylene oxide stream comprised of about 10 mols/hr propylene oxide is recovered overhead via line 15. A portion, about 160 mol/hr, of the bottoms stream from zone 14 passes via line 16 to absorption zone 9 while about 5.5 mols/hr passes via line 19 to separation zone D where water and heavies are separated via line 21 from a recycle isopropanol stream which passes via lines 22 and 1 to zone A; net isopropanol is combined via line 23 with this recycle stream.

The composition of the bottoms stream from zone 14 is about 1.8 ml % acetone, about 56.4 mol % water, about 40.1 mol % isopropanol and about 1.8 mol % heavies.

A vapor purge stream passes via line 8 from epoxidation zone C to absorption zone 9 at the rate of 9.4 mols/hr in order to purge oxygen which is formed in zone C by hydrogen peroxide decomposition. The vapor purge stream comprises about 3.2 mol % oxygen, about 95.7 mol % propylene and about 1.1 mol % propylene oxide.

The liquid bottoms stream from zone 14, cooled to about 40° C., is introduced into the upper section of zone 9 and flows downwardly while the purge vapor from zone C is introduced into the lower section of zone 9. The counter-current vapor liquid contact in zone 9 effectively absorbs propylene and propylene oxide from the purge vapor into the liquid bottoms which is recycled via line 7 to zone C at the rate of about 159 mol/hr as above described.

In order to avoid the formation of a flammable oxygen mixture, methane is introduced into zone 9 via line 17 at the rate of 3 mols/hr and the vapor mixture of methane and oxygen passes via line 3 to oxidation zone A as previously described.

Through practice of the invention, the recovery of propylene is conveniently accomplished without the need for expensive distillation recovery procedures while the hazards of formation of flammable oxygen mixtures is avoided.

In the process description given above, propylene is absorbed from the oxygen/propylene purge stream in an isopropanol and water process stream and this is the preferred practice. Less advantageously, other absorbing liquid streams can be used such as heptane, octane, methanol and acetone.

I claim:

1. In a process for the epoxidation of an olefin with hydrogen peroxide wherein a gas mixture of the olefin and oxygen from hydrogen peroxide decomposition is separated from the liquid epoxidation reaction mixture, the improvement which comprises absorbing the olefin from the gas mixture in a liquid absorbent and adding an inert gas to the oxygen in amount sufficient to prevent formation of flammable gas compositions.

2. The process of claim 1 wherein the olefin is propylene.

3. The process of claim 1 wherein the inert gas is methane.

4. The process of claim 1 wherein the liquid absorbent comprises isopropanol and water.

* * * * *